United States Patent [19]

Firth

[11] 4,275,249

[45] Jun. 23, 1981

[54] PREPARATION OF 2,4-DI-T-ALKYLPHENOL

[75] Inventor: Bruce E. Firth, Arlington Hts., Ill.

[73] Assignee: UOP Inc., Des Plaines, Ill.

[21] Appl. No.: 99,221

[22] Filed: Nov. 30, 1979

[51] Int. Cl.$^3$ .............................................. C07C 37/11
[52] U.S. Cl. ..................................... 568/789; 568/794
[58] Field of Search ................................ 568/789, 794

[56] References Cited

U.S. PATENT DOCUMENTS

| | | | |
|---|---|---|---|
| 3,185,737 | 5/1965 | Geddes | 568/789 |
| 3,290,389 | 12/1966 | Hahn | 568/794 |
| 3,367,981 | 2/1968 | Napolitano | 568/789 |
| 3,670,030 | 6/1972 | Sparks | 568/789 |

*Primary Examiner*—Werren B. Lone
*Attorney, Agent, or Firm*—James R. Hoatson, Jr.; Raymond H. Nelson; William H. Page, II

[57] ABSTRACT

A process for introducing a plurality of alkyl groups into the aromatic ring of a hydroxy-substituted aromatic compound comprises contacting said aromatic compound with an olefin in the presence of alumina or halided alumina as catalyst and recovering the product. When said aromatic compound is phenol, said olefin is isobutylene, and said catalyst is fluorided or chlorided alumina, 2,4-di-t-butylphenol is formed with superior selectivity.

1 Claim, No Drawings

PREPARATION OF 2,4-DI-T-ALKYLPHENOL

BACKGROUND OF THE INVENTION

It has been known for some time that certain hydroxy aromatic compounds are effective antioxidants useful in a wide range of applications. For example, the food additive commonly known as BHA is 2-t-butyl-4-methoxyphenol. Other phenols have been utilized as antioxidants in petroleum products, in plastics, in lubricants, and in other applications where increased oxidative stability is desired. Certain polyalkylated hydroxy-substituted aromatics are especially effective antioxidants. Thus, 2,4-di-t-butylphenol is of commercial utility as an antioxidant when added to fuel oils, such as gasoline. To utilize the antioxidant properties of such compounds it is incumbent to have a method of selectively alkylating hydroxy-substituted aromatic compounds in the position ortho to the hydroxy group.

The methods of alkylating hydroxy-substituted aromatic compounds are legion and well known to the skilled artisan in this field. Those methods based on strong acids, such as phosphoric and sulfuric acids, or strong Lewis acids, such as aluminum chloride, possess the disadvantage that considerable intralmolecular rearrangement, disporportionation, and transalkylation attend the desired alkylation. Thus, the final product using such catalysts tends to reflect thermodynamic control, i.e., given sufficient time an equilibrium mixture will result. For example, monoalkylation of p-cresol with introduction of the group R using the above catalysts may give a mixture of products according to the reaction.

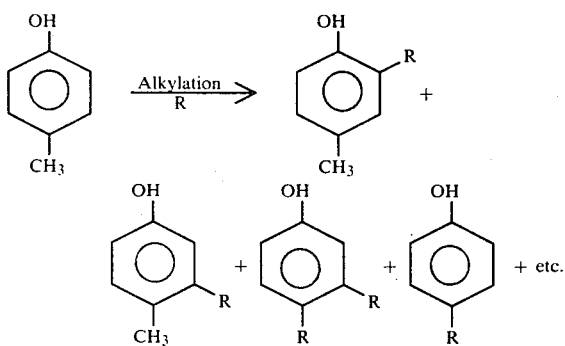

Since an object of the present invention is to provide compounds having at least one alkyl group ortho to the hydroxyl, and since such compounds generally are not thermodynamically more favored than other isomeric alkylated hydroxy-substituted aromatic compounds, the kinds of catalysts described above are unsuitable for efficient synthesis of these products. An additional disadvantage of these catalysts is that the reaction product is a complex mixture of isomers and homologs so that separation of pure components is a difficult if not a near-impossible task.

Use of weaker Lewis acids as catalysts alleviates the problem somewhat. Thus, in U.S. Pat. Nos. 3,290,389 and 3,367,981 are described processes in which alumina is used to alkylate phenols with preferential introduction of alkyl groups at the ortho position. However, because alumina is a relatively weak acid its catalytic activity is low relative to the stronger acids discussed above, necessitating minimum reaction temperatures of about 250° C. and above for several hours to achieve polyalkylation. At these reaction conditions several undesirable side reactions may occur, such as oligomerization of the olefin used as the alkylating agent, thermal cracking to some of the reaction products, and significant disproportionation of some of the alkylated phenols thus formed. All these reactions are undesirable in the context of affording products containing relatively less of those phenols having the greatest antioxidant properties, in the context of affording complex mixtures from which separation of the most desirable component is difficult and tedious, and in the context that one of the reactants is consumed to give useless by-products. Nonetheless, under specified conditions alumina retains a place in the arsenal of available catalysts.

SUMMARY OF THE INVENTION

A principal object of this invention is to provide a process of introducing a plurality of tertiary alkyl groups into the aromatic ring of a hydroxy-substituted aromatic compound with an olefin in the presence of an alumina. An embodiment of this invention comprises the use of this process wherein the alumina contains from about 0.3% to about 5% fluoride ion. Another embodiment of this invention comprises the use of this process wherein the olefin is a terminally disubstituted olefin. Still another embodiment is the process wherein the alumina contains from about 0.3 to about 5% chloride ion.

Other objects and embodiments will be apparent from the description herein.

DESCRIPTION OF THE INVENTION

The alkylation of phenols by olefins in the presence of a catalyst is a reaction of substantial importance. Its use in the preparation of polyalkylated hydroxy-substituted aromatic compounds where the unsubstituted positions of the aromatic ring ortho to the hydroxyl group are preferentially alkylated poses a challenge. On the one hand, use of highly active catalysts tends to lead to thermodynamically controlled mixtures, where the ortho alkylated product is merely one of many components. On the other hand, use of less active catalysts leads to low conversions of the reactants and permits incursion of unwanted side reactions. Another important factor is the recognition that alkylation at the ortho position is sterically hindered. Such steric hindrance is especially important where a tertiary alkyl group is sought to be introduced, for ortho alkylation may be disfavored kinetically as well as thermodynamically.

Alumina, especially in its gamma form, is an attractive compromise as a catalyst for introduction of tertiary alkyl groups. However, the use of alumina to achieve polyalkylation of aromatic compounds with olefins generally requires a temperature in excess of 250° C., and at these temperatures oligomers of the olefin may be formed in substantial amounts. Dialkylation in the presence of alumina normally results in ortho, ortho-dialkylated phenols. However, a discovery of this invention is that ortho, para-dialkylated phenols are the major, if not sole, dialkylation products under reaction conditions where oligomerization of the terminally disubstituted olefin, used as the alkylating agent, is obviated, wholly or in a large part. Alkylation with terminally disubstituted olefins using alumina as catalyst may be done at temperatures from about 150° to about 350° C. and even higher. To minimize oligomerization and dealkylation of reaction products it is preferred that the maximum reaction temperature be about 250° C. The reaction may be conducted at pressures from about 1 to about 250 atmospheres, and even higher, with a reaction time from about 1 to about 20 hours.

Doped alumina is an alumina which has been treated with an inorganic material such that inorganic ions have been deposited therein. Halided alumina is an example of doped alumina, and is an alumina which contains halide ions, said halided alumina being more acidic than alumina itself. In this specification and appended claims, use of the phase "doped alumina" means halided alumina. Although fluoride and chloride are preferred halides, bromide and iodide may be used, although not necessarily with equivalent results.

Another discovery of this invention is that use of halided alumina affords desired products at temperatures of 250° C. and below, i.e., under conditions where oligomer formation and thermal cracking may not occur to any appreciable extent. Additionally, when halided alumina is used, the desired products may be formed with greater specificity than is obtained using alumina itself. A still further advantage of halided alumina is that its greater activity affords substantial energy savings flowing from the lowered requisite reaction temperature.

Fluorided alumina is a product wherein fluoride ions have been deposited in the alumina matrix. It may be prepared, for example, by contacting alumina with a solution of ammonium fluoride, evaporating the water while mixing, and calcining the resulting product. Another mode of preparation, by way of example, is passage of gaseous hydrogen fluoride over solid alumina, wherein the contact time and the total amount of hydrogen fluoride to which the alumina is exposed will determine the final fluoride content of the product. Chlorided alumina may be prepared in a similar fashion. The activity of the halided alumina catalyst in ortho alkylation of phenols depends upon the halogen content of the catalyst as well as the nature of the halogen used. Preparations containing from about 0.3 to about 5 weight percent halogen are preferred, and those from about 0.3 to about 3 weight percent halogen are particularly preferred. When halided alumina is used as a catalyst, reaction temperatures which are employed in the alkylation of a hydroxy-substituted aromatic compound may be from about 250° C. to about 350° C. and even higher, but the maximum reaction temperature is preferably about 250° C. The desirable characteristics of this catalyst permit operation at a pressure from about 1 to about 250 atmospheres and even higher, with a reaction time being from about 1 to about 20 hours. When pressures are desired in excess of those autogenous to the olefin used, a suitable inert gas may be employed, such as nitrogen, helium, and argon, among others.

Another characteristic of, for example, fluorided alumina which may be used advantageously is that it effects dealkylation more readily than alumina. Thus, if 2,4-di-t-butylphenol is heated in the presence of alumina there is formed 4-t-butylphenol by preferential dealkylation of the ortho t-butyl group. This dealkylation occurs with even greater facility and selectivity using fluorided alumina. This characteristic may be used advantageously when the various products of reaction are not to be separated, and when there is a preference for one minor component over another. For example, in the process leading to 2,4-di-t-butylphenol, if there be a preference for 4-t-butylphenol as the major monoalkylated phenol then the use of fluorided alumina, rather than alumina, is highly advantageous.

The process of this invention may be applied to a broad variety of hydroxy-substituted aromatic compounds wherein the aromatic ring may contain one or more other substituents, as aryl, alkyl, aralkyl, alkaryl, hydroxy, alkoxy, aryloxy, alkanoyloxy, amino, alkylamino, arylamino, dialkylamino, diarylamino, mercapto, alkylmercapto, and acylmercapto moieties. The process of this invention may also be applied to said aromatic compounds wherein the aromatic system is a fused-ring aromatic compound, such as naphthalene, anthracene, and the like, which may also bear one or more other substituents such as those enumerated above. Examples of suitable hydroxysubstituted aromatic compounds include the cresols, ethylphenol, butylphenol, hydroquinone, hydroxyanisole, hydroxyaniline, naphthol, methylhydroxybenzoate, methylmercaptophenol, ethylmercaptophenol, phenylmercaptophenol, hydroxydiphenylether, dimethylaminophenol, dibutylaminophenol, and benzylphenol.

Olefins that may be used are of the structural type $R_1R_3C=CHR_2$, where $R_1$ and $R_3$ are selected from the group consisting of an alkyl moiety having from 1 to about 20 carbon atoms, and aryl group such as phenyl, naphthyl, and substituted aryl groups, and where $R_2$ may be selected from the aforementioned group and hydrogen. Examples of terminally disubstituted olefins which may be employed include butylene, the isomeric amylenes, isomeric hexylenes, isomeric heptylenes, isomeric octylenes, isomeric nonylenes, isomeric eicosenes, phenylpropylene, phenylbutylene, etc. More specific examples of such olefins, cited solely for illustrative purposes and not by way of limitation, include isobutylene, 2-methyl-1-butene, 2-methyl-2-butene, 2-ethyl-1-pentene, 2,3,dimethyl-1-butene, 3-methyl-2-pentene, 2-methyl-1-pentene, 2-methyl-2-pentene, 2-phenyl-1-propene, 1,1-diphenylethylene, etc.

Isobutylene is an especially desirable example for the terminally disubstituted olefins used in this invention. Among the compounds which may be made by this process are di-t-butylphenol, tri-t-butylphenol, di-and tri-t-butylphenol, di-and tri-t-amylphenol, di-and tri-t-hexylphenol, di-and tri-t-decylphenol, di-and tri-t-eicosylphenol, 2-t-butyl-4-methylphenol, 2-t-hexyl-4-methylphenol, etc.

The process of this invention may be utilized in the batch mode. For example, a suitable reactor, such as that of the rocking autoclave type, is charged with the desired amount of hydroxy-substituted aromatic compound and halided alumina. Thereupon, the olefin is added, and if it is desired to conduct the reaction at a pressure other than that indigenous to the various components, a suitable inert gas is admitted to the desired pressure. The reactor is sealed, mixing is commenced, and the contents are heated to the predetermined temperature. This reaction temperature is maintained for the time necessary for optimum yield of the alkylated product, generally from about 1 to about 20 hours. After the mixture is cooled, the apparatus is vented, the catalyst is removed by suitable means, for example, by filtration, and product is recovered.

The process of this invention also may be practiced in a continuous mode. A reactor may contain a bed of halided alumina heated and maintained at the desired temperature. A mixture of hydroxy-substituted aromatic compound and olefin may be passed through the bed at a rate such that the total contact time of reactants optimizes the product composition. Olefin and unconverted reactant may be separated from the effluent and recirculated. Product may be recovered from the effluent by suitable means, for example, by distillation.

The following examples illustrate the process described in this invention. It is to be understood that said enumerated olefins and hydroxysubstituted aromatic compounds are merely representative of the class of compounds which may be used and the present invention is not necessarily limited thereto.

All reactions were run in a 300-ml. rocking autoclave. The general procedure was to charge the autoclave with the desired amount of the hydroxysubstituted aromatic compound and the catalyst, following which the olefin used for alkylation was introduced. The reaction mixture was heated to the specified temperature and maintained there for the specified time. When the olefin used was iso-butylene, initial pressures ranged up to about 100 atmospheres. At the end of the reaction, the mixture was allowed to cool and, in the case of gaseous olefins, excess olefin was vented. The catalyst was separated by decantation and filtration, and the composition of the mixture was determined by gas-liquid partition chromatography (glpc).

EXAMPLE 1

A mixture of phenol (25 g, 0.27 mol), isobutylene (1.6 mole, 6-fold excess), and 20 g of alumina was reacted at 250° C. for 4 hours. Examination of the product by glpc showed it consisted of 37% 2,4-di-t-butylphenol, 4% 4-t-butylphenol, 49% 2-t-butylphenol, 4% 2,6-di-t-butylphenol, and 2% 2,4,6-tri-t-butylphenol.

EXAMPLE 2

A mixture of phenol (30 g, 0.32 mole), isobutylene (0.96 mole, 3-fold excess), and 15 g of 1% fluorided alumina was reacted at 250° C. for 3 hours. The product consisted of 2,4-di-t-butylphenol (71%), 2-t-butylphenol (3%), 4-t-butylphenol (17%), and 2,4,6-tri-t-butylphenol (17%). Oligomers were not formed to any appreciable extent. Thus the use of fluorided alumina shows a dramatic improvement in selectivity and overall yield in formation of 2,4-di-t-butylphenol, with the 4-t-butylphenol being the major monoalkylated product, and without significant oligomerization of the olefinic reactant.

EXAMPLE 3

Phenol was alkylated with isobutylene in a continuous process over a fixed bed of chlorided (0.9%) alumina at a liquid hourly space velocity of 0.5, a 4:1 olefin:phenol ratio, and 500 psig. The product composition is tabulated in the accompanying Table.

| TEMPERATURE (°C.) | WEIGHT PERCENT COMPONENTS | | | |
|---|---|---|---|---|
| | 2-t-butylphenol | 4-t-butylphenol | 2,4-di-t-butylphenol | 2,4,6-tri-t-butylphenol |
| 150 | 32 | 1 | 62 | 1 |
| 175 | 16 | 2 | 78 | 2 |
| 200 | 4 | 5.5 | 85 | 3 |
| 225 | 2 | 10 | 77 | 3.5 |
| 250 | 2 | 12 | 55 | 9 |

The Table shows that 2,4-di-t-butylphenol can be formed by alkylation using chlorided alumina as catalyst in excellent yield, with good selectivity, and at a substantially lower temperature than that needed when alumina is employed.

What is claimed is:

1. A process for producing 2,4di-t-butylphenol which comprises reacting phenol and isobutylene at a temperature of from about 150° C. to about 250° C., at a pressure of from about 1 to about 250 atmospheres, and for a period of time of from about 1 to about 20 hours in contact with a catalyst consisting essentially of alumina containing from about 0.3% to about 5.0% fluoride or chloride ion to produce said 2,4-di-t-butylphenol the major product of the process, and recovering the resultant product.

* * * * *